United States Patent [19]
Oosterhof

[11] Patent Number: 5,957,864
[45] Date of Patent: Sep. 28, 1999

[54] ASPIRATION INSTRUMENT FOR CELL BIOPSY PURPOSES

[76] Inventor: Okko Nanning Oosterhof, Boulevard Ir. de Vassy 199, NL-1931 CN, Egmond Aan Zee, Netherlands

[21] Appl. No.: 08/913,447
[22] PCT Filed: Mar. 12, 1996
[86] PCT No.: PCT/NL96/00111
  § 371 Date: Sep. 29, 1997
  § 102(e) Date: Sep. 29, 1997
[87] PCT Pub. No.: WO96/28097
  PCT Pub. Date: Sep. 19, 1996

[30] Foreign Application Priority Data

Mar. 16, 1995 [NL] Netherlands .......................... 9500524

[51] Int. Cl.$^6$ ....................................................... A61B 5/00
[52] U.S. Cl. .......................................... 600/576; 600/562
[58] Field of Search ................................. 600/562, 565, 600/573–576, 579

[56] References Cited

U.S. PATENT DOCUMENTS 4,641,663  2/1987  Juhn ........................................ 128/765
4,766,907  8/1988  de Groot et al. ........................ 600/567

FOREIGN PATENT DOCUMENTS 1111814  3/1956  France .

*Primary Examiner*—Max Hindenburg
*Attorney, Agent, or Firm*—Young & Thompson

[57] ABSTRACT

Aspiration instrument for cell biopsy purposes, comprising: a cylinder (3) which at the distal end is provided with a region for fastening a hypodermic needle (5), a plunger (6) whose distal end is in the form of a piston (8), which piston is movable in the cylinder between a first position and a second position, a guide (4) for guiding the plunger, a pre-compression element (17) for pre-compressing the plunger in the direction of the first position, which pre-compression element is activated when the plunger is moved from the first to the second position, locking elements (9, 10) for locking the plunger in the second position, a device for unlocking the locking elements, in order to make the plunger move from the second to the first position under the influence of the pre-compression elements. The plunger, the guide for the plunger, the pre-compression element, the locking elements and the unlocking device are all combined to form a unit (2) to which the cylinder is detachably connected. The unit is made of sterilizable material.

11 Claims, 1 Drawing Sheet

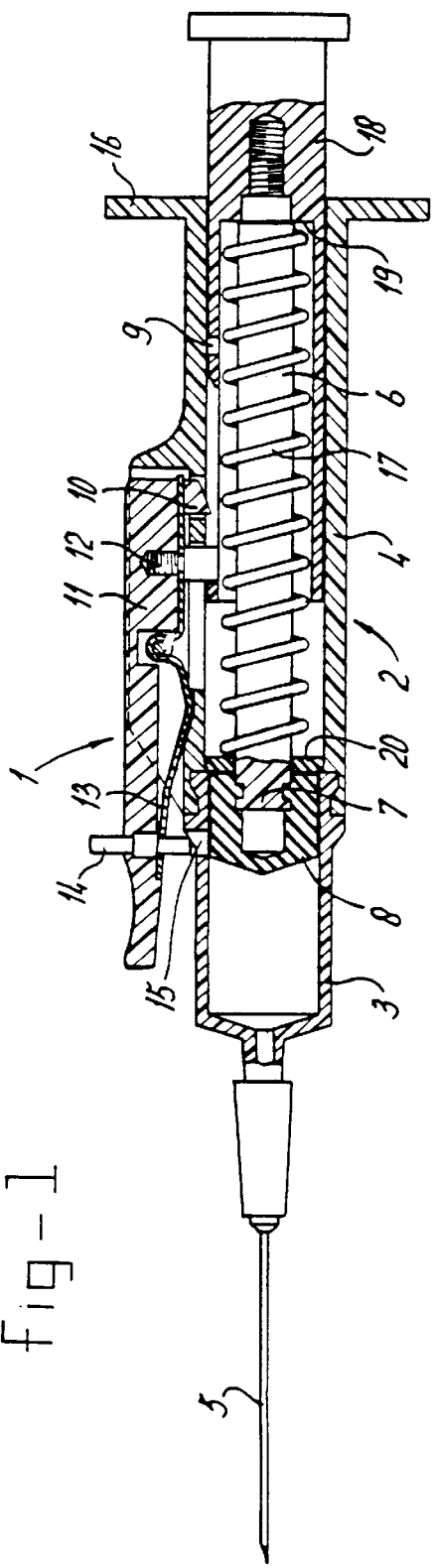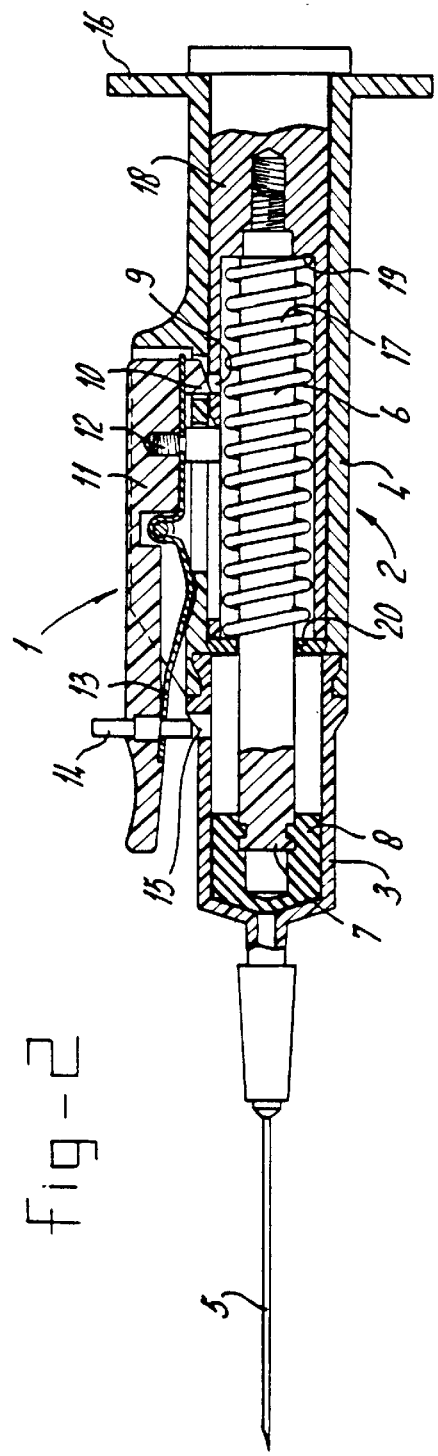

ASPIRATION INSTRUMENT FOR CELL BIOPSY PURPOSES

FIELD OF THE INVENTION

The present invention relates to an aspiration instrument for cell biopsy purposes, comprising:

a cylinder which at the distal end is provided with means for fastening a hypodermic needle, a plunger whose distal end is in the form of a piston, which piston is movable in the cylinder between a first position and a second position, guide means for guiding the plunger, pre-compression means, by means of which the plunger is pre-compressible in the direction of the first position, which pre-compression means are activated when the plunger is moved from the first to the second position, locking means by means of which the plunger can be locked in the second position, means for unlocking the locking means, in order to make the plunger move from the second to the first position under the influence of the pre-compression means.

BACKGROUND OF THE INVENTION

Such an aspiration instrument is known in practice and is described in a brochure obtainable from Cooper Companies Inc., established at One Bridge Plaza, Fort Lee, N.J. 07024, USA. The known aspiration instrument is designed for the collection of cell material from subcutaneous tissue for purposes of cytological research. The known aspiration instrument is made ready for use by fastening a hypodermic needle to the cylinder and subsequently depressing the plunger against the force of the pre-compression means until the plunger is locked in the second position. During this process pre-compression means are pre-compressed. The piston is now situated at the distal end of the cylinder. The hypodermic needle can then be introduced into the tissue to be examined, following which the locking can be undone simply by a finger movement. Under the influence of the compressed pre-compression means, the plunger—and thus the piston—moves back to the first position, while a partial vacuum is created in the cylinder, as a result of which cell tissue is aspirated. When sufficient cell tissue has been collected, the partial vacuum in the front part can be neutralized by deforming the piston by means of a pawl and consequently admitting air to the cylinder.

In the case of the known aspiration instrument the partial vacuum is created beforehand, so that the person performing the biopsy, called the doctor below, can then concentrate fully on the collection of the cell material. The known aspiration instrument in this case can be operated with one hand, with the result that the collection of the cell material can be accurate and the doctor can advantageously use the other hand for, for example, fixing the tissue to be examined during the operation. Moreover, the working distance from the hand to the tissue to be punctured is short, with the result that the operation can be performed with a high degree of accuracy.

However, the known aspiration instrument is designed for a single use. In practice, this means that the aspiration instrument has been found too expensive for human applications, and certainly for veterinary applications. Due to the relatively high wastage of material involved in single use, the known aspiration instrument is also environmentally unfriendly. Besides, in various countries there are different procedures for the collection of cell material, which in practice can mean that it is compulsory to collect cell material twice from one patient. This even further emphasizes the abovementioned drawbacks of the known aspiration instrument.

The object of the present invention is to provide an aspiration instrument of the type mentioned at the beginning which does not have the above mentioned disadvantages, while at the same time the above mentioned advantages are retained.

SUMMARY OF THE INVENTION

To this end, the aspiration instrument according to the invention is characterized in that the plunger, the guide means for the plunger, the pre-compression means, the locking means and the unlocking means therefor are combined to form a unit to which the cylinder is detachably connected, while the unit is made of sterilizable material.

An aspiration instrument in which a cylinder can be detachably connected at one side is known from U.S. Pat. No. 4,967,762, which describes a system of a hypodermic syringe and a cylinder in which a needle can be fixed. The cylinder is for detachably fastening on the front of the hypodermic syringe. This system has the disadvantage that it cannot be operated with one hand. For the collection of cell material, the needle is introduced into the tissue to be punctured, following which the plunger has to be pulled backwards in order to create sufficient partial vacuum in the cylinder to be able to aspirate the cell material. This is an ergonomically paradoxical manoeuvre. During the withdrawal of the piston from a hypodermic syringe a tensed-up position of the hand occurs, which makes sensitive and controlled guidance of the needle of the hypodermic syringe difficult. Besides, this movement requires the use of two hands, with the result that the tissue to be punctured cannot be fixed in the correct position. All this increases the chance of unrepresentative cell material also being collected. The reliability of the diagnosis in regard to the collected material is consequently adversely affected.

In one advantageous embodiment, the unit and the cylinder are connected to each other by means of a bayonet fastening. This embodiment makes it possible to fasten the cylinder and the unit of the aspiration instrument according to the invention to each other in a simple and secure manner.

In another advantageous embodiment, the unit and the cylinder are connected to each other by means of a threaded fastening. This embodiment is an alternative possibility for fastening the cylinder quickly and securely to the unit.

In a further advantageous embodiment, the volume determined in the cylinder between the first and the second position is at least approximately equal to 2.5 cc. In this embodiment an optimum is advantageously found between the maximum partial vacuum to be created in the cylinder, on the one hand, and the length of the aspiration instrument, on the other hand. It has been found in practice that with a greater volume of cylinder the partial vacuum which it is possible to create therein increases only marginally. In addition, at this length the aspiration instrument according to the invention can be easily operated with one hand; the working distance between the hand and the tissue to be punctured permits accurate handling of the aspiration instrument.

In another embodiment of the aspiration instrument according to the invention, at least the guide means are made of metal, in particular of aluminum. In this embodiment the guide means can be sterilized after use, following which they are ready for reuse. In addition, the metal makes a detailed machining of the aspiration instrument possible during the manufacturing process. The metal is preferably an aluminum alloy. In this embodiment the unit is easy to handle, which increases the accuracy with which the cell material can be collected. At the same time, this means that the unit is of durable construction, which results in a cost saving in the long term.

In a further advantageous embodiment, the piston is fastened detachably on a piston holder connected to the remaining part of the plunger. In this embodiment, it is possible to fasten the previously sterilized piston quickly and securely on the piston holder in such a way that in use no leakage of cell material from the cylinder occurs.

The present invention also relates to a cylinder which at one end has means for fastening a hypodermic needle and at the other end is provided with means for connecting the cylinder to the unit according to the invention.

The piston is preferably fastened in the cylinder with the aid of locking means. This design makes it possible to connect both the cylinder and the piston simultaneously to the unit.

BRIEF DESCRIPTION OF THE DRAWINGS

The present invention will be illustrated further below with reference to the appended drawings, in which FIG. 1 shows a sectional view of an aspiration instrument according to the present invention, in which the plunger is situated in the first position;

FIG. 2 shows a sectional view of the aspiration instrument according to the invention, in which the plunger is situated in the second position.

DETAILED DESCRIPTION OF THE INVENTION

FIG. 1 shows a sectional view of aspiration instrument 1 according to the present invention. Aspiration instrument 1 comprises a unit 2 to which a cylinder 3 is detachably connected. Unit 2 comprises a plunger 6 which is movable with the aid of guide means 4 from a first to a second position in the direction of cylinder 3. In FIG. 1 plunger 6 is shown in the first position. One end 7 of the plunger is in the form of a piston holder and is provided with a piston 8. During the forward movement of the plunger 6, piston 8 moves through the cylinder 3 from the first to a second position.

In FIG. 2 aspiration instrument 1 is likewise shown in longitudinal section, in this case plunger 6 being situated in the second position. It can be seen clearly that piston 8 is now situated in the second position, in the front of the cylinder 3.

Unit 2 is also provided with locking means for locking plunger 6 in the second position. To this end, in the preferred embodiment shown, plunger 6 comprises opening 9, which is suitable for accommodating lug 10. The locking means can be unlocked with the aid of unlocking means. In the preferred embodiment shown, both the locking means and the unlocking means are fitted on a lever 11, which is fastened to unit 2.

During the depression of plunger 6, pre-compression means 17 for moving plunger 6 back to the first position are pre-compressed, which means are situated in the unit 2. In the preferred embodiment shown, the pre-compression means 17 consist of a coil spring which is fitted around the plunger 6, and at one side rests against wall 20 of the unit 2 and at the other side rests against a supporting part 19 in plunger 6. Unlocking the locking means with the aid of unlocking lever 11 causes plunger 6 to move from the second to the first position.

In the preferred embodiment shown, the guide means are in the form of a tube 4. The tube 4 is shut off at its distal end by a wall 20, in which an opening is made, in order to allow through the plunger 6. Plunger 6 is also provided with a part 18, which is preferably detachably fastened thereto, and whose external dimensions correspond to the internal dimensions of tube 4. In the preferred embodiment shown, the part 18 comprises a supporting part 19 against which coil spring 17 rests.

Lever 11 is preferably attached to unit 2 by means of the mechanism shown, in which pawl 12 of unit 2 can be accommodated in a corresponding opening on lever 11. Lever 11 is provided with spring means 13, preferably in the form of a leaf spring, which ensure that the lever 11 springs back into its top position. Lever 11 is provided at the front side with a preferably movable pawl 14, which can be accommodated in opening 15 on cylinder 3. The way in which the above works will be explained below.

Cylinder 3 is preferably made of a plastic material, for example polycarbonate. Cylinder 3 is provided at its distal end with means for fastening hypodermic needle 5, which means preferably comprise a Luer lock. At the proximal end the cylinder 3 is provided with fastening means for detachable connection thereof to the unit 2. These fastening means, which are situated partially on the unit 2, can comprise, for example, a bayonet closure or a screw closure (not shown). In this way cylinder 3 can be connected detachably to the unit 2 and forms the disposable part of the aspiration instrument 1 according to the present invention. Cylinder 3 is sterilized and supplied in a sterile pack, and is manufactured in accordance with the guidelines for medical aids of the particular countries where the product is to be sold under the CE standard. The internal volume of the cylinder 3, which is determined by the first and second position of piston 8, is approximately 2.5 cc in the preferred embodiment. This makes the creation of a theoretical partial vacuum or underpressure of approx. 900 mbar possible according to the law of Boyle—Gay Lussac. It is known from practice that increasing this volume in fact contributes little more to the increase in the partial vacuum. However, the extension of cylinder 3, and thus of aspiration instrument 1, increases the working distance between the tissue to be punctured and the hand of the doctor. With the choice of this volume, the length of the aspiration instrument is therefore determined in the optimum way.

The unit 2 is made of a material which is suitable for sterilization. Unit 2, which comprises the mechanism, can thus be reused many times, which increases the environmental friendliness of aspiration instrument 1. Unit 2 is preferably made partially or fully of metal. In a second preferred embodiment, at least the guide means are made of metal. The metal is preferably an aluminum alloy, which makes unit 2 light and durable. Unit 2 can be, for example, cast or obtained by mechanical working.

Piston 8 and piston holder 7 are formed in such a way that piston 8 can be clamped detachably on piston holder 7. Piston 8 and piston holder 7 are formed in such a way here that leakage of the aspirated cell material from cylinder 3 is prevented. After attachment, piston 8 is clamped at the sides by cylinder 3. Piston 8 is preferably made of a flexible material, for example plastic.

The coil spring 17 is preferably made of stainless steel material and has a spring constant which is adapted to the work which is necessary for travelling the distance from the second position to the first position. The chosen spring constant depends partly on the friction resistance encountered during the distance to be travelled. This friction resistance is partly determined by two components: the piston 8 and the inside wall of cylinder 3. In order to reduce the resistance, piston 8 is preferably made of a self-lubricating plastic, such as that in known hypodermic syringes. In the preferred embodiment discussed, the spring constant is 0.385 N/mm, with a tolerance of ±0.1. It will be clear that this value is given only by way of indication, and is in no way intended as a restriction.

The aspiration instrument according to the present invention can be operated as follows:

First of all, the sterilized cylinder 3, which is supplied separately, is removed from the pack. Piston 8 is preferably already fitted in a locked position in cylinder 3. For this purpose, piston 8 contains locking means, such as a thickened part in the outside wall thereof which fits into a recess in the inside wall of cylinder 3. The thickened part is preferably designed in such a way that in use it will break off on movement of piston 8 from the first to the second position in cylinder 3. Cylinder 3 and piston 8 are then connected to unit 2 together in one movement with the aid of fastening means, preferably a bayonet closure, whereby piston 8 is fastened on piston holder 7.

As an alternative to the method of operation described above, a sterilized piston 8, delivered separately, can be removed from its pack and fastened on piston holder 7. The cylinder 3, which has also been sterilized, is then removed from its pack and connected by means of the fastening means to the unit 2 of the aspiration instrument 1. Finally, in both cases hypodermic needle 5 is fitted on cylinder 3. The aspiration instrument 1 is now fully ready for use.

The doctor who is going to collect the cell material must first of all depress the plunger 6, in which case counterpressure can be given by the index and middle finger by placing these fingers behind wings 16 of unit 2. The doctor in this case has one hand available for firmly fixing the tissue location to be punctured and then with the other hand introducing needle 5 of the aspiration instrument 1 into the tissue to be examined.

After the point of the needle 5 has been introduced into the suspect tissue, the partial vacuum can be activated by pressing on the front of the unlocking lever 11. For this, only a very subtle downward movement of the index finger is required. In the course of this, lug 10 is lifted out of opening 9 of unit 2, with the result that the pre-compression means for moving plunger 6 back to the first position are activated. During this backward movement, a partial vacuum is created in cylinder 3, with the result that cell material is sucked up through needle 5. In the course of this, the doctor has to perform a number of to and fro movements with needle 5 through the suspect tissue. When sufficient cell material has been collected, the partial vacuum in cylinder 3 must first be removed before needle 5 is withdrawn from the patient's skin. This is necessary in order to prevent cell material which is not relevant from also being aspirated during the withdrawal of needle 5. The partial vacuum can also be removed by exerting pressure on lever construction 11. Pawl 14 will in this case deform piston 8 by way of opening 15 in cylinder 3, in which case the pressure in cylinder 3 is neutralized. For this purpose, lever 11 must be held in its lowest position for a few seconds. Needle 5 can then be withdrawn from the tissue, and the collected cell material is available for examination.

Aspiration instrument 1 is held like a pen during the entire operation. The short working distance between the manipulating hand and the tissue to be punctured contributes to the optimum sensitivity of the aspiration instrument according to the invention.

Cylinder 3 and piston 8 can be thrown away together with needle 5 after use, while the unit 2 can be sterilized or autoclaved. In the preferred embodiment shown, unit 2 is simple to dismantle prior to sterilization. By in fact dividing the aspiration instrument into two parts, a small part as the disposable part and the larger part as the non-disposable part, wastage of material is largely prevented. The relatively most expensive part and most material-consuming part can be reused many times.

I claim:

1. In an aspiration instrument for cell biopsy purposes, comprising:

a cylinder which at the distal end is provided with means for fastening a hypodermic needle, a plunger having a piston at its distal end, which piston is movable in the cylinder between a first position and a second position, guide means for guiding the plunger, pre-compression means by means of which the plunger is pre-compressible in the direction of the first position, which pre-compression means are activated when the plunger is moved from the first to the second position, locking means by means of which the plunger can be locked in the second position, means for unlocking the locking means, in order to make the plunger move from the second to the first position under the influence of the pre-compression means, the improvement wherein the plunger, the guide means for the plunger, the pre-compression means, the locking means and the unlocking means therefor are combined to form a single unit to which the cylinder provided with the piston is detachably connected, said unit being made of sterilizable material, and wherein the plunger is provided with a piston holder at its distal end for detachable connection with said piston.

2. Aspiration instrument according to claim 1, wherein the unit and the cylinder are connected to each other by means of a bayonet fastening.

3. Aspiration instrument according to claim 1, wherein the unit and the cylinder are connected to each other by means of a threaded fastening.

4. Aspiration instrument according to claim 1, wherein the guide means are in the form of a tube which is shut off at the distal end by a wall, in which an opening is made, in order to allow through the plunger, and the plunger is also provided with a part whose external dimensions correspond go the internal dimensions of the tube, which part is guided in the tube.

5. Aspiration instrument according to claim 4, wherein the pre-compression means consist of a coil spring which is disposed around the plunger, and at one side rests against said wall and at the other side rests against a supporting part in the part of the plunger.

6. Aspiration instrument according to claim 5, wherein in the first position the piston rests against the wall.

7. Aspiration instrument according to claim 1, wherein at least the guide means are made of metal.

8. Aspiration instrument according to claim 1, wherein the volume determined in the cylinder between the first and the second position is at least approximately equal to 2.5 cc.

9. Aspiration instrument according to claim 7, wherein the guide means are made of an aluminum alloy.

10. Cylinder having at one end means for fastening a hypodermic needle, and at the other end means for detachably connecting the cylinder to a unit made of sterilizable material and comprised of a plunger, guide means for the plunger, pre-compression means, first locking means, and unlocking means therefor; said plunger having a piston at its distal end which in use moves in the cylinder, and a piston holder for detachable connection to the piston.

11. Cylinder according to claim 10, in which the piston is fastened with the aid of second locking means.

* * * * *